(12) United States Patent
Alvarez

(10) Patent No.: US 10,874,139 B2
(45) Date of Patent: Dec. 29, 2020

(54) E-VAPOR DEVICE INCLUDING CAPSULE CONTAINING PRE-VAPOR FORMULATION

(71) Applicant: Altria Client Services Inc., Richmond, VA (US)

(72) Inventor: David Alvarez, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 479 days.

(21) Appl. No.: 14/792,764

(22) Filed: Jul. 7, 2015

(65) Prior Publication Data

US 2017/0006917 A1 Jan. 12, 2017

(51) Int. Cl.
| | |
|---|---|
| *A24F 40/42* | (2020.01) |
| *A24F 47/00* | (2020.01) |
| *A61M 15/06* | (2006.01) |
| *A61M 15/00* | (2006.01) |
| *A61M 11/04* | (2006.01) |

(52) U.S. Cl.
CPC .......... *A24F 40/42* (2020.01); *A24F 47/008* (2013.01); *A61M 15/003* (2014.02); *A61M 15/06* (2013.01); *A61M 11/042* (2014.02); *A61M 15/0035* (2014.02)

(58) Field of Classification Search
None
See application file for complete search history.

(56) References Cited

U.S. PATENT DOCUMENTS

| | | | | |
|---|---|---|---|---|
| 3,906,950 A | * | 9/1975 | Cocozza | A61M 15/0028 128/203.15 |
| 3,948,264 A | * | 4/1976 | Wilke | A61M 15/0028 128/203.15 |
| 4,423,724 A | * | 1/1984 | Young | A61M 15/0033 128/203.15 |
| 7,578,298 B2 | | 8/2009 | Karles et al. | |
| 8,156,944 B2 | * | 4/2012 | Han | H05B 3/42 |
| 8,689,803 B2 | | 4/2014 | Gonda | |
| 2003/0150454 A1 | * | 8/2003 | Burr | A61M 15/0028 128/203.21 |

(Continued)

FOREIGN PATENT DOCUMENTS

| | | | | |
|---|---|---|---|---|
| WO | WO-2011107104 A1 | * | 9/2011 | ............ A61M 15/06 |
| WO | WO 2015071703 | * | 5/2015 | |

OTHER PUBLICATIONS

"Get started with Intellicig Electronic Cigarettes", www.intellicig. com/get-started, 2014, pp. 1-2, Intellicig.

*Primary Examiner* — Joseph S Del Sole
*Assistant Examiner* — Manley L Cummins, IV
(74) *Attorney, Agent, or Firm* — Harness, Dickey & Pierce, P.L.C.

(57) ABSTRACT

An e-vapor device may include a capsule, a mouthpiece configured to receive the capsule, and a vaporizer configured to engage with the mouthpiece to enclose the capsule therebetween. The capsule is configured to hold a pre-vapor formulation therein. The vaporizer is configured to pierce the capsule to access the pre-vapor formulation therein and to heat the pre-vapor formulation to generate a vapor. Additionally, the vaporizer may be configured to cease a heating of the pre-vapor formulation when a current in the heater structure is less than a reference level. Accordingly, the occurrence of an unpleasant taste resulting from overheating may be reduced or prevented.

20 Claims, 2 Drawing Sheets

(56) References Cited

U.S. PATENT DOCUMENTS

| | | | |
|---|---|---|---|
| 2004/0025865 A1* | 2/2004 | Nichols | A61M 11/042 128/200.14 |
| 2007/0074721 A1* | 4/2007 | Harmer | A61M 15/0028 128/203.15 |
| 2010/0006113 A1* | 1/2010 | Urtsev | A24F 47/008 131/273 |
| 2011/0005535 A1* | 1/2011 | Xiu | A24F 47/008 131/273 |
| 2011/0114671 A1* | 5/2011 | Harrison | A61J 1/00 128/203.15 |
| 2011/0265806 A1* | 11/2011 | Alarcon | A24F 47/00 131/273 |
| 2012/0260927 A1 | 10/2012 | Liu | |
| 2012/0325228 A1 | 12/2012 | Williams | |
| 2013/0056005 A1* | 3/2013 | Knudsen | A61M 15/06 128/202.21 |
| 2014/0190496 A1* | 7/2014 | Wensley | A24F 47/008 131/273 |
| 2014/0224249 A1 | 8/2014 | Landry | |
| 2015/0040929 A1* | 2/2015 | Hon | A24F 47/008 131/329 |
| 2015/0230522 A1* | 8/2015 | Horn | A24F 47/008 131/329 |
| 2017/0135402 A1* | 5/2017 | Zitzke | A24F 47/008 |
| 2017/0273914 A1* | 9/2017 | Knudsen | A61K 36/81 |

\* cited by examiner

E-VAPOR DEVICE INCLUDING CAPSULE CONTAINING PRE-VAPOR FORMULATION

BACKGROUND

Field

The present disclosure relates to electronic vapor devices including sealed containers of pre-vapor formulation.

Description of Related Art

Electronic vapor devices are electrically-powered articles configured to heat a pre-vapor formulation for the purpose of producing a vapor for subsequent inhalation by an adult vaper. Electronic vapor devices may also be referred to as e-vapor devices or e-vaping devices. Generally, an e-vapor device includes a reservoir configured to hold the pre-vapor formulation, a wick that is arranged in communication with the pre-vapor formulation, a heating element that is arranged in thermal proximity to the wick, and a power source configured to supply electricity to the heating element. The heating element may be in a form of a relatively thin wire that is coiled a plurality of times around the wick. When a current is supplied to the heating element during the operation of the e-vapor device, the wire undergoes resistive heating to vaporize the pre-vapor formulation in the wick to produce a vapor for subsequent inhalation by an adult vaper.

Some e-vapor devices include a first section coupled to a second section via a threaded connection. The first section may be a replaceable cartridge, and the second section may be reusable. The threaded connection may be a combination of a male threaded member on the first section and a female threaded receiver on the second section. The first section may include an outer tube (or housing) extending in a longitudinal direction and an inner tube within the outer tube. The inner tube may be coaxially positioned within the outer tube. The second section may also include the outer tube (or housing) extending in a longitudinal direction. The e-vapor device may include a central air passage defined in part by the inner tube and an upstream seal. The reservoir may be configured to optionally include a storage medium that is operable to store the pre-vapor formulation therein. The reservoir may be contained in an outer annulus between the outer tube and the inner tube. The outer annulus is sealed by the seal at an upstream end and by a stopper at a downstream end so as to prevent leakage of the pre-vapor formulation from the reservoir. The reservoir, pre-vapor formulation, wick, and heating element may be contained in the replaceable first section, and the power source may be contained in the reusable second section. Accordingly, the first section may be discarded as a whole and replaced when the pre-vapor formulation therein is depleted.

SUMMARY

An e-vapor device may include a capsule, a mouthpiece configured to receive the capsule, and a vaporizer configured to engage with the mouthpiece to enclose the capsule therebetween. The capsule is configured to hold a pre-vapor formulation therein. The vaporizer is configured to pierce the capsule to access the pre-vapor formulation therein and to heat the pre-vapor formulation to generate a vapor. The e-vapor device may further include a body section configured to engage with the vaporizer. The body section may include a power source.

The capsule may be hermetically-sealed. Additionally, the capsule may have an interior volume of 100 μL or less. The capsule may be configured to hold 100 mg or less of the pre-vapor formulation. Furthermore, the capsule may be spherically-shaped. For example, the capsule may be in a form of a bead with an outer barrier formed of a food grade material. The food grade material may be silicone. In another instance, the capsule may be conically-shaped. The capsule may be in a form of a pod with a puncture seal.

The mouthpiece includes a recess configured to receive the capsule. The recess may include a concave surface that corresponds to an outer surface of the capsule.

The vaporizer may include a puncture device with a pointed, proximal end and an opposing distal end. The puncture device may be a hollow, elongated structure defining a channel therein that extends from the pointed, proximal end to the opposing distal end. The puncture device may be configured to protract and pierce the capsule when the mouthpiece is engaged with the vaporizer and to retract when the mouthpiece is disengaged from the vaporizer.

The vaporizer may also include a wick that extends through the channel from the pointed, proximal end to the opposing distal end of the puncture device. The end portions of the wick may protrude from the pointed, proximal end of the puncture device. The wick may have a length of about 15 mm or less.

The vaporizer may further include a heater structure that is wrapped around a portion of the wick adjacent to the distal end of the puncture device. To mitigate the risk of overheating, the vaporizer may be configured to cease a heating of the pre-vapor formulation when a current in the heater structure is less than a reference level.

A method of operating an e-vapor device may include measuring a current in a heater structure of the e-vapor device. Additionally, the method may include ceasing a supply of power to the heater structure when the current is measured to be less than a reference level. Accordingly, the occurrence of an unpleasant taste resulting from overheating may be reduced or prevented.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
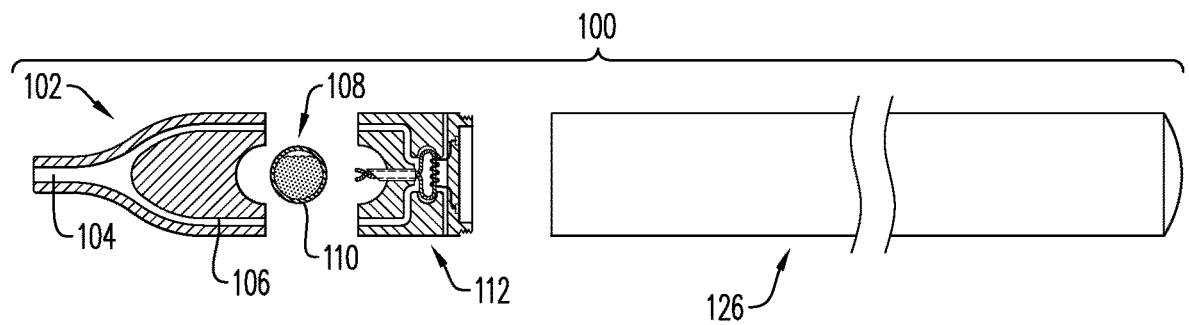
FIG. 1 is an exploded, cross-sectional view of an e-vapor device according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is an exploded, cross-sectional view of an e-vapor device according to an example embodiment. Referring to FIG. 1, an e-vapor device 100 includes a mouthpiece 102 that is configured to receive a capsule 108. The mouthpiece 102 includes a proximal end and an opposing distal end. The proximal end of the mouthpiece 102 is configured to release the vapor generated by the e-vapor device 100, while the distal end of the mouthpiece 102 is configured to engage with the vaporizer 112. The distal end of the mouthpiece 102 may taper towards the proximal end. The taper may be such that the proximal end has a flattened shape or a more pointed, nozzle-type shape, although example embodiments are not limited thereto.

The mouthpiece 102 includes a recess at the distal end that is configured to receive the capsule 108. The recess may include a concave surface that corresponds to an outer surface of the capsule 108. As a result, a majority (or all) of the concave surface may be contacted by an outer surface of the capsule 108 when the capsule 108 is seated in the recess. For example, when the capsule 108 has a spherical shape, the concave surface of the recess may have a shape of a partial sphere (e.g., hemisphere) to enhance a seating of the capsule 108 therein. When the concave surface is hemispherically-shaped, the depth of the recess may be about equal to the radius of the capsule 108 (when spherically-shaped) such that the recess is configured to receive about half of the capsule 108. In this non-limiting embodiment, about half of the capsule 108 may be hidden from view, while the other half may be visible when the capsule 108 is initially seated in the recess (and before the mouthpiece 102 is connected to the vaporizer 112).

However, it should be understood that the depth to which the capsule 108 is received in the recess of the mouthpiece 102 may be less or more than the radius of the capsule 108. In one instance, the curvature of the concave surface of the recess may be less than a hemisphere such that the depth to which the capsule 108 is received in the recess is less than the radius of the capsule 108. In another instance, the recess may initially extend into the distal end of the mouthpiece 102 in a linear manner before terminating with a hemispherical surface so as to resemble a shallow bore hole with a rounded bottom. In such an example embodiment, the diameter of the recess will be constant at an outer linear portion of the recess and will decrease at an inner hemispherical portion of the recess. The depth of such a recess will be greater than the radius of the capsule 108 but less than the diameter of the capsule 108, although example embodiments are not limited thereto.

The capsule 108 may be held in the recess of the mouthpiece 102 via a friction-fit. The friction-fit may be sufficient to keep the capsule 108 from falling out of the recess when the mouthpiece 102 is tilted such that the recess faces downward toward the ground. The friction-fit may be achieved via a relatively close size correspondence between the recess and the portion of the capsule 108 seated therein. The friction-fit may also be achieved (or supplemented) with an additional material (e.g., polymer material) that is disposed at the distal end of the mouthpiece 102. In one example, the additional material may be in the form of a relatively thin film that coats the surface of the recess so as to provide (or enhance) the requisite friction to hold the capsule 108. In the another example, the additional material may be in the form of a polygonal or cylindrical body that is inserted into a cavity at the distal end of the mouthpiece 102, wherein the polygonal or cylindrical body defines the recess for receiving the capsule 108. In such a non-limiting embodiment, the capsule 108 may be seated in the polygonal or cylindrical body, which is held by the mouthpiece 102.

The recess of the mouthpiece 102 may be additionally provided with gripping structures to help hold the capsule 108. The gripping structures may be in the form of bumps, nodules, ridges, and/or other suitable raised portions on the surface of the recess adjacent to the rim. The gripping structures may be provided periodically (e.g., as two to three evenly-spaced bumps) or continuously (e.g., as an annular ridge) around the mouth of the recess. When the above-discussed additional material (for friction-fit) is present, the gripping structures may be formed as an integral part of this additional material.

The gripping structures in the recess of the mouthpiece 102 may be retractable to enhance the ease of insertion and/or removal of the capsule 108. In an example embodiment, the gripping structures may be in the form of a plurality of ball structures that are disposed in pockets within the mouthpiece 102 and spring-loaded so as to protrude from corresponding openings in the surface of the recess when in a protracted position. The openings in the surface of the recess are smaller than the corresponding ball structures in order to retain the ball structures in their respective pockets. In such a non-limiting embodiment, only a portion (as opposed to an entirety) of the ball structures will protrude therefrom as a result of being biased by a spring (or biased with a resilient equivalent). When a capsule 108 is inserted into the recess, the ball structures will retract into their corresponding pockets via compression of the springs therein. The stored energy of the compressed springs will, in turn, exert a force on the capsule 108 via the ball structures so as to help grip and hold the capsule 108 in the recess.

It should be understood that the option for retractable gripping structures is not limited to the above-discussed ball structures and, instead, may come in a variety of different forms. For example, an elongated structure (e.g., short rod) may also be used as a retractable gripping structure. The elongated structure may have a rounded end that is configured to protrude from an opening in the surface of the recess to contact the capsule 108. The elongated structure is spring-biased (or biased with a resilient equivalent) and will retract and deform the spring when the capsule 108 is inserted into the recess. With regard to the deformation, the spring may be arranged (e.g., behind the elongated structure) such that the elongated structure will retract and compress the spring when the capsule 108 is inserted into the recess. In another non-limiting embodiment, the spring may be arranged (e.g., with the elongated structure extending therethrough) such that the elongated structure will retract and lengthen the spring when the capsule 108 is inserted into the recess. The stored energy of the deformed spring will, in turn, exert a force on the capsule 108 via the rounded end of the elongated structure so as to help grip and hold the capsule 108 in the recess.

To release the capsule 108, a button-actuated lever arrangement may be provided to further retract the elongated structure such that the rounded end no longer contacts the capsule 108. In such a non-limiting embodiment, a lever may be connected to an inner end of the elongated structure that is opposite to the rounded end. A button arrangement may be connected to an opposing end of the lever that is not connected to the inner end of the elongated structure. When the button arrangement is pressed, the lever will pivot and retract the elongated structure so as to release the grip on the capsule 108 in the recess. The elongated structure may be biased (e.g., via compression or lengthening of a resilient structure) so as to default to a protracted state for the rounded end when the button arrangement is not pressed.

To aid the removal of the capsule 108 from the recess of the mouthpiece 102, a dislodging structure may be arranged at the base of the recess. The dislodging structure may include an elongated structure (e.g., rod) that is configured to protract into the recess to unseat a capsule 108 therein. The elongated structure may be aligned lengthwise so as to coincide with a central longitudinal axis of the e-vapor device 100 when the mouthpiece 102 is connected to the vaporizer 112, although example embodiments are not limited thereto. The dislodging structure may additionally include a button-actuated lever arrangement that is configured to protract the elongated structure into the recess so as to dislodge the capsule 108 therefrom. In such a non-limiting embodiment, a lever may be connected to an inner end of the elongated structure that is opposite to the end that will contact the capsule 108. A button arrangement may be connected to an opposing end of the lever that is not connected to the inner end of the elongated structure. When the button arrangement is pressed, the lever will pivot and protract the elongated structure into the recess so as to dislodge the capsule 108 (e.g., depleted capsule) therefrom. The elongated structure may be biased (e.g., via compression or lengthening of a resilient structure) so as to default to a retracted state when the button arrangement is not pressed. When in the retracted state, the elongated structure may be completely withdrawn into the body of the mouthpiece 102 such that the capsule 108 (e.g., new capsule) can be fully seated in the recess during loading. The button-actuated lever arrangement may be configured to simultaneously retract the gripping structures while protracting the elongated structure of the dislodging structure into the recess to facilitate a removal of the capsule 108 therefrom.

A plurality of vapor channels 106 extend into the mouthpiece 102 from the distal end. The plurality of vapor channels 106 (e.g., 2, 3, or 4 vapor channels) converge within the mouthpiece 102 to form a vapor outlet 104 that exits at the proximal end of the mouthpiece 102. The plurality of vapor channels 106 may commence from a rim surface of the distal end that surrounds the recess and continue within the mouthpiece 102 so as to follow the contours of the outer surface of the mouthpiece 102. The positioning of the plurality of vapor channels 106 may be in an evenly-spaced arrangement. The shape of each of the plurality of vapor channels 106 may be tube-like so as to have a circular cross-section. In another instance, the shape of each of the plurality of vapor channels 106 may be more flattened and belt-like so as to have a cross-section that resembles a slit.

However, it should be understood that example embodiments are not limited to the above configurations. Rather, the plurality of vapor channels 106 may have various placements and configurations depending on the type of vapor that will pass therethrough as well as the intended usage of the sub-surface and interior space of the mouthpiece 102. For instance, the placement and configuration of the plurality of vapor channels 106 may be designed to accommodate the presence of various components (e.g., button-actuated lever arrangement) within the mouthpiece 102. Furthermore, although a plurality of vapor channels 106 are shown in FIG. 1, it should be understood that the mouthpiece 102 may alternatively include just one vapor channel 106 that transitions into the vapor outlet 104.

The mouthpiece 102 may be secured to the vaporizer 112 via a snap-fit type or other suitable arrangement. For instance, the mouthpiece 102 or the vaporizer 112 may include a mating member while the other structure includes a corresponding recess that is configured to receive the mating member so as to establish a snap-fit connection between the mouthpiece 102 and the vaporizer 112. The engagement of the mating member with the corresponding recess may result in an audible click, which notifies the adult vaper that a proper connection has been established.

A twist-lock type arrangement may also be used to connect the mouthpiece 102 to the vaporizer 112. In such an arrangement, the mouthpiece 102 or the vaporizer 112 may include a threaded, rotatable sleeve that is configured to rotate and engage a corresponding thread on the other structure so as to unite the mouthpiece 102 and the vaporizer 112. The rotatable sleeve may be internally or externally threaded and configured to rotate while the mouthpiece 102 and the vaporizer 112 remain stationary relative to each other.

In another instance, a magnetic arrangement may be used to connect the mouthpiece 102 to the vaporizer 112. In such a non-limiting embodiment, a first magnet may be arranged in the mouthpiece 102, and a second magnet may be arranged in the vaporizer 112. The first and/or second magnets may be exposed or hidden from view behind a layer of material. The first and second magnets are oriented so as to be attracted to each other, and a plurality of pairs of the first and second magnets may be provided to ensure a secure connection and proper alignment between the mouthpiece 102 and the vaporizer 112. However, it should be understood that the present disclosure is not limited to the above examples and that other arrangements may alternatively be used to connect the mouthpiece 102 to the vaporizer 112.

In an example embodiment, the mouthpiece 102 is a semi-permanent component that is intended for multiple use while providing the option for voluntary replacement by an adult vaper. For instance, the mouthpiece 102 may, in addition to its intended functionality, provide a visual or other sensory appeal to the adult vaper. In particular, the mouthpiece 102 may be formed of an ornamental material and/or include designs. The ornamental material used to fabricate the mouthpiece 102 may be a wood, metal, glass, ceramic, plastic, or a combination thereof. The designs on the mouthpiece 102 may include patterns, images, characters, color schemes, or a combination thereof. Additionally, the designs may be formed from an aesthetic arrangement of the ornamental materials that are used to fabricate the mouthpiece 102. Thus, the mouthpiece 102 may be customized so as to provide an expression of personality and individuality by an adult vaper.

The capsule 108 is configured to hold a pre-vapor formulation therein. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol. In a non-limiting embodiment, the pre-vapor formulation may be an e-liquid.

The pre-vapor formulation may be hermetically-sealed within the capsule 108 so as to be isolated from the surrounding environment. Additionally, an interior volume of the capsule 108 may be about 100 μL or less. The pre-vapor formulation may fill a substantial portion (e.g., 70% or more) of the interior volume of the capsule 108. In an example embodiment, the capsule 108 is configured to hold about 100 mg or less of the pre-vapor formulation. The capsule 108 may also be spherically-shaped. The material used to form the capsule 108 may have sufficient strength and/or resilience to allow the capsule 108 to substantially hold its shape rather than deform under its own weight. For instance, the capsule 108 may be in a form of a bead with an outer barrier 110 that is formed of a food grade material. The standards for a food grade material are as set forth by the pertinent regulatory authorities (e.g., U.S. Food & Drug Administration (FDA)). The food grade material may be silicone, although example embodiments are not limited thereto.

The vaporizer 112 is configured to engage with the mouthpiece 102 so as to enclose the capsule 108 therebetween. For instance, the vaporizer 112 may also include a recess that will align with the recess of the mouthpiece 102 to form a chamber that will house the capsule 108. The vaporizer 112 is configured to pierce the capsule 108 to access the pre-vapor formulation therein and to heat the pre-vapor formulation to generate a vapor. The piercing of the capsule 108 may occur after the vaporizer 112 is engaged with the mouthpiece 102. In another instance, the piercing of the capsule 108 may occur simultaneously with the engagement of the vaporizer 112 to the mouthpiece 102. The e-vapor device 100 is configured such that the vapor generated by the vaporizer 112 will be directed into the vapor channels 106 and out of the vapor outlet 104 of the mouthpiece 102 for inhalation by an adult vaper.

The e-vapor device 100 further includes a body section 126 that is configured to engage with the vaporizer 112. The first end of the vaporizer 112 is configured to engage with the mouthpiece 102, while the opposing second end of the vaporizer 112 is configured to engage with the body section 126. In an example embodiment, the opposing second end of the vaporizer 112 may have external threads that are structured to mate with the internal threads of the body section 126. As a result, the external threads at the opposing second end of the vaporizer 112 will not be visible when the vaporizer 112 is fully engaged (e.g., via clockwise rotation) with the body section 126. The vaporizer 112 may be separated from the body section 126 by rotating the vaporizer 112 in the opposite direction (e.g., counterclockwise) to unmate the external threads of vaporizer 112 from the internal threads of the body section 126. Alternatively, the opposing second end of the vaporizer 112 may have internal threads that are structured to mate with the external threads of the body section 126.

It should be understood that the connection between the vaporizer 112 and the body section 126 is not limited to the above-discussed threaded arrangement. Rather, other suitable arrangements may be used to unite the vaporizer 112 and the body section 126. For example, a snap-fit, twist-lock, and/or magnetic arrangement (as discussed supra in relation to the engagement of the mouthpiece 102 and the vaporizer 112) may be used to achieve the connection between the vaporizer 112 and the body section 126.

The body section 126 may include a power source therein. In an example embodiment, the power source may be a battery. For instance, the battery may be a lithium-ion battery or a variant thereof (e.g., lithium-ion polymer battery). The battery may also be a nickel-metal hydride battery, a nickel-cadmium battery, a lithium-manganese battery, a lithium-cobalt battery, or a fuel cell. The e-vapor device 100 is usable until the energy in the power source is depleted, after which the power source will need to be replaced. Alternatively, the power source may be rechargeable and include circuitry allowing the power source to be charged with an external charging device. In this rechargeable embodiment, the circuitry, when charged, provides power for a desired or pre-determined number of puffs, after which the circuitry must be re-connected to the external charging device.

The e-vapor device 100 may also include control circuitry including a puff sensor. The puff sensor is configured to sense an air pressure drop and to initiate the application of a voltage from the power source to the heater structure in the vaporizer 112. Additionally, the control circuitry may include a heater activation light that is configured to glow when the heater structure is activated. The heater activation light may include an LED. The heater activation light can also be configured to allow temporary deactivation by an adult vaper in the interest of privacy, such that the heater activation light will not activate during vaping.

When the puff sensor is activated, the control circuitry may automatically supply power to the heater structure in the vaporizer 112. The time period of the electric current supply to the heater structure may be pre-set or designated depending on the amount of pre-vapor formulation desired to be vaporized. The control circuitry may be programmable for this purpose. The control circuitry may supply power to the heater structure as long as the puff sensor detects a pressure drop. Alternatively, the control circuitry may include a manual switch for an adult vaper to initiate a puff. In such a non-limiting embodiment, the control circuitry may supply power to the heater structure for a pre-set or desired time period when the switch is pressed by an adult vaper. In another instance, the control circuitry may continue to supply power to the heater structure for as long as the switch is in the "ON" position.

Figure 2:
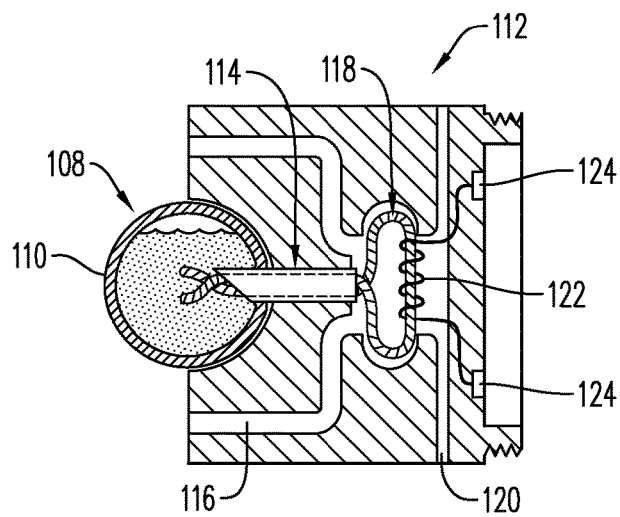
FIG. 2 is a cross-sectional view of the capsule as pierced by the vaporizer of FIG. 1.

FIG. 2 is a cross-sectional view of the capsule as pierced by the vaporizer of FIG. 1. Referring to FIG. 2, the vaporizer 112 includes a puncture device 114 that is configured to pierce the capsule 108. The puncture device 114 includes a pointed, proximal end and an opposing distal end. In an example embodiment, the puncture device 114 is a hollow, elongated structure that defines a channel therein that extends from the pointed, proximal end to the opposing distal end. For instance, the puncture device 114 may resemble a hypodermic needle. The vaporizer 112 may also include a recess that is configured to receive the capsule 108. Additionally, the gripping structures discussed above in connection with the recess of the mouthpiece 102 may be similarly applied to the recess of the vaporizer 112. When the mouthpiece 102 is engaged with the vaporizer 112, the recess of the mouthpiece 102 may be aligned with the recess of the vaporizer 112 so as to form a chamber with an interior volume and shape that substantially corresponds to the size and contours of the capsule 108. Thus, when the capsule 108 has a spherical shape, the chamber may also have a spherical shape, although example embodiments are not limited thereto. As a result, the capsule 108 may be securely contained within the e-vapor device 100.

The puncture device 114 may protrude from the base of the recess of the vaporizer 112. To facilitate a piercing of the capsule 108, the puncture device 114 may be oriented orthogonally from the base of the recess of the vaporizer 112 so as to coincide with a central longitudinal axis of the e-vapor device 100. The exposed length of the puncture device 114 may be less than the depth of the recess of the vaporizer 112 (although the overall length of the puncture device 114 may be longer than the depth of the recess). In such a non-limiting embodiment, the puncture device 114 will not extend beyond the rim of the recess of the vaporizer 112. The puncture device 114 may be a stationary structure relative to the recess of the vaporizer 112. As a result, the capsule 108 may be simultaneously pierced by the puncture device 114 as it is seated in the recess of the vaporizer 112.

Alternatively, the puncture device 114 may be a tractable structure relative to the recess of the vaporizer 112. For instance, the puncture device 114 may initially be in a retracted position within the vaporizer 112 so as to not protrude into the recess. In such a retracted position, a capsule 108 can be seated in the recess of the vaporizer 112 without being pierced by the puncture device 114. After the mouthpiece 102 is engaged with the vaporizer 112 (thereby enclosing the capsule 108 therebetween), the puncture device 114 may be manually protracted to pierce the capsule 108. The puncture device 114 may be arranged as part of a sliding assembly in order to achieve the protraction. An externally-accessible knob may be attached to the puncture device 114 such that the externally-accessible knob and the puncture device 114 are configured to move together in a longitudinal direction, relative to the e-vapor device 100. In a non-limiting embodiment, the knob (which is externally-accessible to an adult vaper) may be configured to move along a guide path, wherein one end of the guide path corresponds to a retracted position for the puncture device 114, while the opposing end of the guide path corresponds to a protracted position for the puncture device 114. A side notch may optionally be provided at the ends of the guide path to receive the knob (via a circumferential movement of the knob), thereby providing a locking arrangement to help ensure that the puncture device 114 remains in the desired protracted or retracted position. Such a locking arrangement may be analogous to a door sliding bolt assembly.

In another instance, the puncture device 114 may be spring-loaded and actuated with a button-actuated lever arrangement. For example, as a result of the spring bias (or bias from another suitable resilient structure), the puncture device 114 may default to a protracted position. The arrangement includes a button that (when pressed by an adult vaper) displaces a lever which, in turn, deforms the spring so as to retract the puncture device 114. The spring may be arranged behind the distal end of the puncture device 114 or arranged so as to spiral around the length of the puncture device 114, although example embodiments are not limited thereto. In addition to retracting the puncture device 114, the button-actuated lever arrangement may also simultaneously retract any gripping structures that may have optionally been provided in the recess of the vaporizer 112. Releasing the button of the arrangement (e.g., after engaging the mouthpiece 102 with the vaporizer 112) will allow the spring to return to its original shape, which will also cause the puncture device 114 to protract (e.g., so as to pierce the capsule 108 if present).

Conversely, the puncture device 114 may be spring-loaded and configured to default to a retracted position. In such an example, pressing the button of the arrangement will extend and lock the puncture device 114 in the protracted position. When the puncture device 114 is in the protracted position, the spring (or other suitable resilient structure) will be deformed. Pressing the button of the arrangement again will unlock and retract the puncture device 114 via the release of the stored energy of the deformed spring as the spring returns to its original shape. In a non-limiting embodiment, the button-actuated arrangement may include a first cam, a second cam, a guide pin, a ratchet spring, and a button spring.

The first cam may include first right-angled teeth and may be configured to move along the guide pin to interact with the second cam. The second cam is rotatable and may include second right-angled teeth that are configured to mate with the first right-angled teeth of the first cam. The second right-angled teeth of the second cam include alternating deep (or through-hole) furrows and shallow furrows that are configured to receive the guide pin. When the button of the arrangement is pressed, the angled edge of the first teeth of the first cam will push on the angled edge of the second teeth of the second cam to unseat the guide pin from the existing furrow of the second cam. When the guide pin clears the vertical edge of the existing furrow, the angled edge of the second teeth of the second cam will slide relative to the angled edge of the first teeth of the first cam (as a result of being biased by the ratchet spring) such that the second cam will rotate to seat the guide pin in the next furrow. The first cam will also separate from the second cam as a result of being biased by the button spring. When the guide pin is seated in a deep (or through-hole) furrow of the second cam, the puncture device 114 may be in a retracted position. On the other hand, when the guide pin is seated in a shallow furrow of the second cam, the puncture device 114 may be in a locked, protracted position. Thus, pressing the button of the arrangement will alternate the puncture device 114 between the retracted position and the locked, protracted position. In a non-limiting embodiment, the button-actuated arrangement for protracting, locking, and retracting the puncture device 114 may be analogous to the mechanism for a retractable pen.

In another example embodiment, the puncture device 114 may be configured to protract and pierce the capsule 108 when the mouthpiece 102 is engaged with the vaporizer 112 and to retract when the mouthpiece 102 is disengaged from the vaporizer 112. For instance, the timing of the protracting and retracting of the puncture device 114 may coincide with the timing of the engagement and disengagement, respectively, of the mouthpiece 102 and the vaporizer 112 (e.g., so as to occur simultaneously). In such an example, the vaporizer 112 may include a lever arrangement therein that is configured to maneuver the puncture device 114 between a retracted position and a protracted position. The lever arrangement may be biased with a spring (or other suitable resilient structure) such that the puncture device 114 will default to the retracted position. The lever arrangement may be accessible for actuation via an access opening in the surface of the rim surrounding the recess of the vaporizer 112. A first end of a lever of the arrangement may be connected to the distal end of the puncture device 114, while the opposing second end may be aligned with the access opening. The mouthpiece 102 may include an actuating pin that is configured for insertion into the access opening of the vaporizer 112.

When the mouthpiece 102 is engaged with the vaporizer 112, the actuating pin of the mouthpiece 102 will insert into the access opening of the vaporizer 112 and press against the second end of the lever of the vaporizer 112 so as to pivot the puncture device 114 to the protracted position. The pivoting of the lever will result in the deformation of the spring. On the other hand, when the mouthpiece 102 is disengaged from the vaporizer 112, the actuating pin of the mouthpiece 102 will move away from the second end of the lever of the vaporizer 112 (which, in turn, will cause the lever to pivot back to its original position via the spring) so as to allow the puncture device 114 to default to the retracted position.

A wick 118 is arranged to extend through the puncture device 114 via the channel therein so as to protrude from both the pointed, proximal end and the opposing distal end. In an example embodiment, the end portions of the wick 118 may protrude from the pointed, proximal end of the puncture device 114 as two free ends, while the middle portion of the wick 118 may protrude from the opposing distal end in the form of a loop. Alternatively, the wick 118 may be configured such that only one free end protrudes from the pointed, proximal end of the puncture device 114, while the other free end is secured (e.g., knotted) to a portion of the wick 118 that is adjacent to the opposing distal end of the puncture device 114 so as to form a loop.

The portion(s) of the wick 118 protruding from the pointed, proximal end of the puncture device 114 may have a protruding length that is sufficient to allow the protruding portion(s) of the wick 118 to contact an inner surface of the outer barrier 110 so as to increase the amount of the pre-vapor formulation that is drawn from the capsule 108. During vaping, the pre-vapor formulation within the capsule 108 will be depleted so as to eventually only cover a minor portion of the inner surface of the outer barrier 110. As a result, a wick 118 that will bend over (e.g., from the weight of the pre-vapor formulation drawn therein) so as to follow the decreasing supply of the pre-vapor formulation down to the inner surface of the outer barrier 110 of the capsule 108 may help to draw out the remaining residual amount of the pre-vapor formulation from the capsule 108. Optionally, assuming that the remaining residual amount of the pre-vapor formulation in the capsule 108 will tend to pool in the vicinity of the puncture device 114 (due to the orientation of the e-vapor device 100 during vaping), the pointed, proximal end of the puncture device 114 may include one or more perforations (or slit-like grooves) through which the free end(s) of the wick 118 may pass to increase the likelihood that the wick 118 will be in fluidic communication with the remaining residual amount of the pre-vapor formulation in the capsule 108.

The wick 118 may have a total length of about 15 mm or less. A shorter length for the wick 118 may be beneficial in that less of the pre-vapor formulation from the capsule 108 will be required therein for purposes of keeping the wick 118 adequately saturated. As a result, with a wick 118 having a relatively short length, more of the pre-vapor formulation from the capsule 108 may be available for generating a vapor. Moreover, the puncture device 114 may be configured to have a piercing depth that is just adequate to introduce the channel at the pointed, proximal end beyond the outer barrier 110 so as to reduce the length that will be needed for the wick 118. The outer barrier 110 of the capsule 108 is sufficiently durable so as to not rupture or break apart when pierced by the puncture device 114. Furthermore, the outer barrier 110 of the capsule 108 may be sufficiently resilient so as to grip the pointed, proximal end of the puncture device 114 when pierced so as to be substantially leak-proof when the pre-vapor formulation is drawn out of the capsule 108 by the wick 118.

The wick 118 may be constructed of a fibrous and flexible material. The fibrous and flexible material may be in the form of at least one filament having a capacity to draw the pre-vapor formulation into the wick 118. For example, the wick 118 may include a bundle of filaments, such as glass (or ceramic) filaments. In another instance, the wick 118 may include a bundle comprising a group of windings of glass filaments (e.g., three of such windings). The wick 118 may include filaments having a cross-section which is generally cross-shaped, clover-shaped, Y-shaped, or in another suitable shape. The wick 118 is configured to draw the pre-vapor formulation thereinto via capillary action as a result of the interstitial spacing between the filaments. The capillary properties of the wick 118, combined with the properties of the pre-vapor formulation, can be tailored to ensure that the pre-vapor formulation will be adequately present in the wick 118 in the area of the heater structure 122 to avoid overheating.

A heater structure 122 is arranged in thermal contact with the wick 118 to enable the heating of the pre-vapor formulation therein. For instance, the heater structure 122 may be wrapped around a portion of the wick 118 that is adjacent to the distal end of the puncture device 114. The heater structure 122 is configured to heat the pre-vapor formulation contained in the wick 118 to a temperature sufficient to vaporize the pre-vapor formulation and form a vapor. The heater structure 122 may be coiled around the wick 118 at least three times, although example embodiments are not limited thereto.

Suitable electrically resistive materials for the heater structure 122 may include titanium, zirconium, tantalum, and metals from the platinum group. Examples of suitable metal alloys include stainless steel, nickel-, cobalt-, chromium-, aluminum-, titanium-, zirconium-, hafnium-, niobium-, molybdenum-, tantalum-, tungsten-, tin-, gallium-, manganese-, and iron-containing alloys, and super-alloys based on nickel, iron, cobalt, and stainless steel. For instance, the heater structure 122 may include nickel aluminides, a material with a layer of alumina on the surface, iron aluminides, and other composite materials. The electrically resistive material may optionally be embedded in, encapsulated, or coated with an insulating material or vice-versa, depending on the kinetics of energy transfer and the external physicochemical properties required. In a non-limiting embodiment, the heater structure 122 includes at least one material selected from the group consisting of stainless steel, copper, copper alloys, nickel-chromium alloys, superalloys, and combinations thereof. In another non-limiting embodiment, the heater structure 122 includes nickel-chromium alloys or iron-chromium alloys. Furthermore, the heater structure 122 may include a ceramic portion having an electrically resistive layer on an external surface thereof. A higher resistivity for the heater structure 122 lowers the current draw or load on the power source.

The ends of the heater structure 122 are connected to electrical contacts 124. In an example embodiment, one end of the heater structure 122 is connected to an electrical contact 124 which corresponds to a positive terminal of a power source (e.g., battery), while the opposing end of the heater structure 122 is connected to another electrical contact 124 which corresponds to a negative terminal of the power source. When a current is supplied to the heater structure 122 via the electrical contacts 124, heat is generated by Joule heating (as a result of the passage of the current therethrough), which is also referred to in the art as ohmic heating or resistive heating. In particular, an electric current passing through the heater structure 122 encounters resistance (opposition to the passage of the electric current therethrough), thus resulting in the heating of the heater structure 122.

When activated, the heater structure 122 in the vaporizer 112 may heat a portion of the wick 118 surrounded by the heater structure 122 for less than about 10 seconds (e.g., less than about 7 seconds). Thus, the power cycle (or maximum puff length) can range from about 2 seconds to about 10 seconds (e.g., about 3 seconds to about 9 seconds, about 4 seconds to about 8 seconds, or about 5 seconds to about 7 seconds), although example embodiments are not limited thereto.

During vaping, air may be drawn into the vaporizer 112 through the air inlets 120. A puff sensor may be arranged in connection with the air inlets 120 so as to initiate the application of a voltage from the power source to the heater structure 122 when a puff from an adult vaper is sensed. In an example embodiment, the air inlets 120 may lead to a chamber from which the vapor channels 116 originate. The heater structure 122 may be arranged in the chamber. As a result of the puff from an adult vaper, the vapor (generated from the heating of the pre-vapor formulation in the wick 118 by the heater structure 122) will be drawn through the vapor channels 116 toward the mouthpiece 102. The mouthpiece 102 is configured to engage with the vaporizer 112 such that the vapor channels 106 of the mouthpiece 102 will align with the vapor channels 116 of the vaporizer 112 to form a continuous channel for conveyance of the vapor. The various considerations and aspects discussed supra with regard to the vapor channels 106 of the mouthpiece 102 may also apply to the vapor channels 116 of the vaporizer 112.

At times, the wick 118 will not be saturated with the pre-vapor formulation. Although not limited to the following situations, the sub-saturation levels of the pre-vapor formulation in the wick 118 may be because (1) the pre-vapor formulation in the capsule 108 has been depleted, (2) the pre-vapor formulation in the capsule 108 is not (or no longer) accessible to the wick 118, or (3) a capsule 108 was not loaded in the e-vapor device 100. Vaping with (and, thus, heating) a sub-saturated wick 118 may result in an experience that is less than appealing (e.g., unpleasant taste) due to an overheating of the wick 118 and/or the residual pre-vapor formulation therein.

To reduce or prevent the occurrence of overheating, the temperature of the wick 118 and/or the heater structure 122 may be monitored. Additionally, because conductance and resistance are temperature-dependent, these properties and/or other related variables may also be monitored to reduce or prevent the occurrence of overheating. For instance, because the resistance of a metal may increase with temperature, the vaporizer 112 may be configured to cease a heating of the pre-vapor formulation when a current in the heater structure 122 is less than a reference level. Additional and more in-depth examples will be subsequently discussed below.

Figure 3:
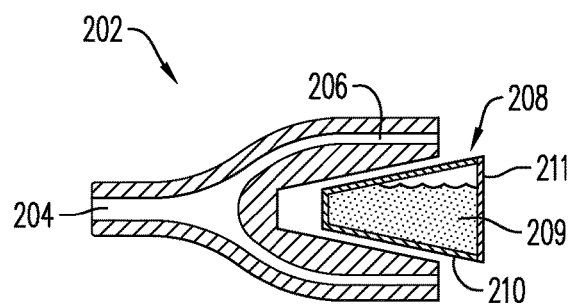
FIG. 3 is a cross-sectional view of a mouthpiece and a capsule configured to be inserted therein according to an example embodiment.

FIG. 3 is a cross-sectional view of a mouthpiece and a capsule configured to be inserted therein according to an example embodiment. Referring to FIG. 3, the mouthpiece 202 is configured to receive a capsule 208. The capsule 208 is configured to hold a pre-vapor formulation 209 therein and may be frustoconically-shaped or conically-shaped, although other suitable shapes may also be used (e.g., cylindrically-shaped, polygonally-shaped). The recess of the mouthpiece 202 may be a frustoconical cavity or a conical cavity to enhance a fit of the capsule 208 therein, although it should be understood that the contours of the recess can be varied to accommodate whatever shape the capsule 208 may have.

The seating, securing, and dislodging of the capsule 208 in the recess of the mouthpiece 202 may be as discussed supra in connection with the seating, securing, and dislodging of the capsule 108 in the recess of the mouthpiece 102. For instance, the capsule 208 may be held in the recess of the mouthpiece 202 via a friction-fit. A mating arrangement may also be provided, wherein the sidewall of the recess of the mouthpiece 202 may include a mating member (e.g., retractable, spring-loaded ball structure) while the side surface of the capsule 208 includes a corresponding recess that is configured to receive the mating member. In another instance, a magnetic arrangement may be provided to hold the capsule 208 in the recess of the mouthpiece 202. In such a non-limiting embodiment, a first magnet may be arranged in the base of the recess of the mouthpiece 202, and a second magnet may be arranged in the tapered end of the capsule 208. The first and/or second magnets may be exposed or hidden from view behind a layer of material. The first and second magnets are oriented so as to be attracted to each other. A dislodging structure may be optionally provided to help separate the first magnet from the second magnet when the capsule 208 is to be removed from the recess of the mouthpiece 202.

The vapor outlet 204 and the vapor channel 206 in FIG. 3 may correspond to the vapor outlet 104 and the vapor channel 106, respectively, in FIG. 1. As a result, the various considerations and aspects discussed supra in connection with the vapor outlet 104 and the vapor channel 106 may also be applicable to the vapor outlet 204 and the vapor channel 206. Additionally, the mouthpiece 202 may be configured to engage with a vaporizer (e.g., vaporizer 112), as discussed supra in connection with the mouthpiece 102.

The capsule 208 may be in a form of a pod 210 with a puncture seal 211. The pod 210 and the puncture seal 211 may be configured to hermetically seal the pre-vapor formulation 209 therein. The headspace, if present in the capsule 208, may be filled with an inert gas, although example embodiments are not limited thereto. The puncture seal 211 may be pierced with a puncture device (e.g., puncture device 114) in order to access the pre-vapor formulation 209 in the capsule 208. The puncture seal 211 of the capsule 208 is sufficiently durable to allow penetration without rupturing or breaking apart (e.g., so as to spill the pre-vapor formulation 209 therein) when pierced by the puncture device. Furthermore, the puncture seal 211 of the capsule 208 may be sufficiently resilient so as to grip the pointed, proximal end of the puncture device when pierced so as to be substantially leak-proof when the pre-vapor formulation 209 is drawn out of the capsule 208 by the wick (e.g., wick 118).

Figure 4:
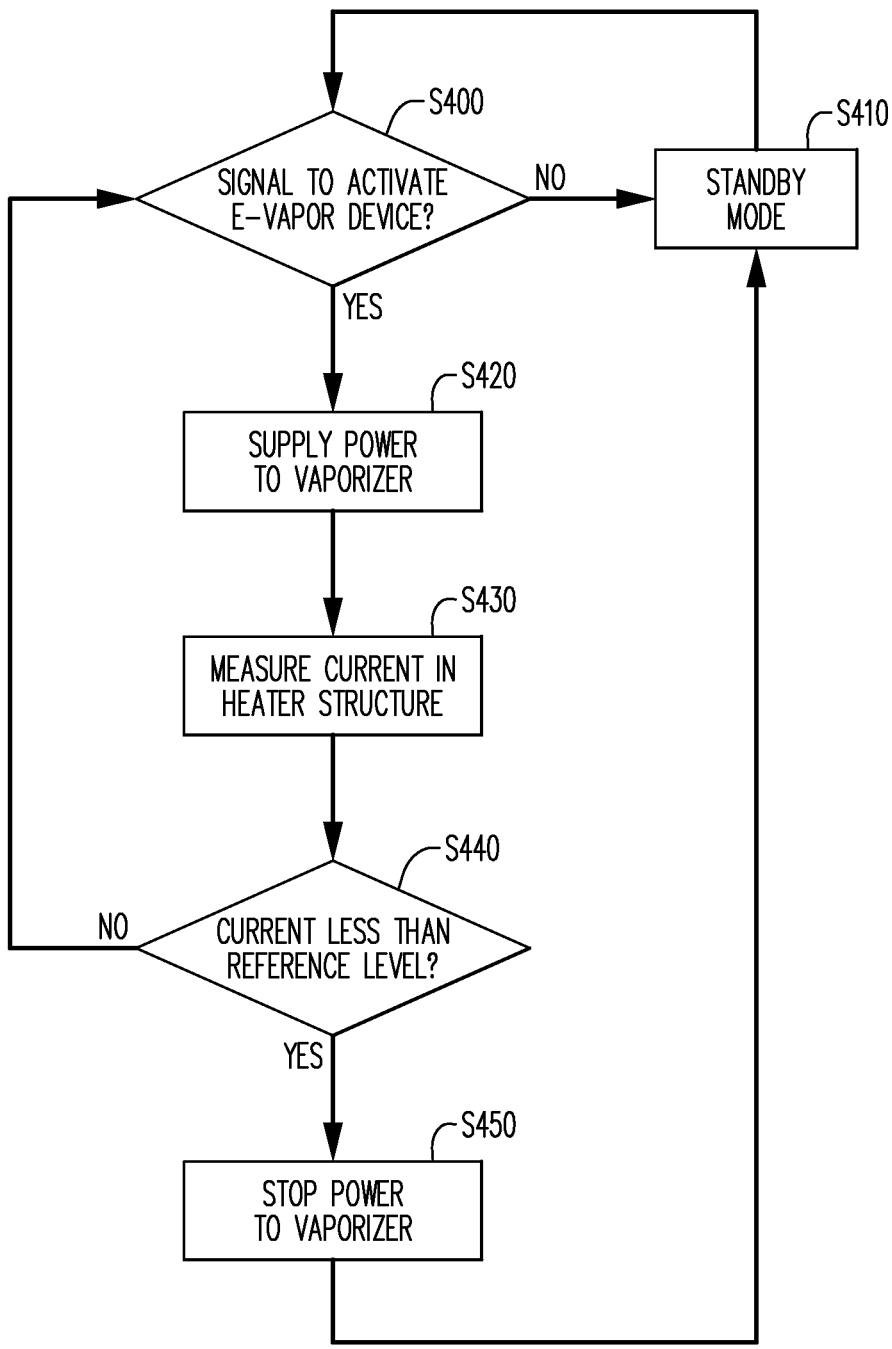
FIG. 4 is a flow chart of a method of operating an e-vapor device according to an example embodiment.

FIG. 4 is a flow chart of a method of operating an e-vapor device according to an example embodiment. The method of operating may be designed to reduce or prevent the occurrence of overheating as a result of the wick (e.g., wick 118) being less than adequately saturated with a pre-vapor formulation (e.g., due to the capsule being depleted and in need of replacement). For instance, a method of operating an e-vapor device (e.g., e-vapor device 100) may include measuring a current in a heater structure (e.g., heater structure 122) of the e-vapor device. The method may additionally include ceasing a supply of power to the heater structure when the current is measured to be less than a reference level.

Referring to FIG. 4, an e-vapor device may be may be configured to perform steps S400 to S450, along with other steps or actions that may be pertinent to the method discussed herein. The steps may be achieved with the appropriate combination of known sensors, processors, and other relevant circuit components, as would be understood by those of ordinary skill in the art based on the teachings herein.

In the activating step S400 of FIG. 4, a determination may be made as to whether a signal has been received to activate the e-vapor device for vaping. In an example embodiment, the signal may be from a puff sensor. If no signal has been received, then the e-vapor device will remain in standby mode (or transition to standby mode, e.g., such as when an adult vaper has stopped vaping) in accordance with the standby step S410. The e-vapor device may remain in standby mode until a signal to activate has been received. Thus, e-vapor device may be configured to passively await a signal to activate.

When a signal to activate the e-vapor device has been received, then power is supplied to the vaporizer in accordance with the powering step S420. In accordance with the measuring step S430, the current in the heater structure of the vaporizer may also be measured. The current in the heater structure of the vaporizer may be an indirect indicator of the temperature of the heater structure.

Resistance and resistivity are temperature-dependent properties, wherein the resistance and resistivity of a material may increase with temperature. When the resistance and resistivity of a material increase, the amount of current passing through the material will decrease. As a result, the amount of current passing through a material may be correlated with the temperature of the material. In an example embodiment, the amount of current corresponding to a threshold temperature (above which overheating will occur) may be set as a reference level of current. The threshold temperature and reference level of current may be determined by experimentation. As noted above, because the resistance and resistivity of a material may increase with temperature and consequently decrease the amount of current passing therethrough, a measured current that is less than the reference level of current may mean that the temperature has exceeded the threshold temperature and, thus, presents an overheating risk.

In the comparing step S440 of FIG. 4, a determination is made as to whether the measured current (from measuring step S430) is less than the reference level of current. If the measured current is not less than the reference level of current (thus suggesting that the threshold temperature has not yet been exceeded), then vaping will be permitted to continue as long as a signal continues to be received to activate the e-vapor device (in accordance with the activating step S400). On the other hand, if the measured current is less than the reference level of current (thus suggesting that the threshold temperature has been exceeded), then the power to the vaporizer is stopped in accordance with the stopping step S450, and the e-vapor device will transition to standby mode in accordance with the standby step S410. Attempts by an adult vaper to just continue vaping (e.g., even though the wick is not adequately saturated because the capsule is depleted) will merely result in a prompt return to standby mode in accordance with the standby step S410. Vaping can be resumed once the appropriate measures are taken to adequately saturate the wick with a pre-vapor formulation (e.g., replacement of the depleted capsule with a new capsule). Accordingly, the risk of overheating, which may result in an experience that is less than appealing (e.g., unpleasant taste), may be reduced or prevented.

Alternatively, rather than measuring current, the resistance and/or resistivity of the heater structure may be measured to indirectly determine the temperature of the heater structure. For instance, the resistance R of a conductor of uniform cross section can be expressed as $$R = \rho \frac{L}{A},$$

where $\rho$ is the resistivity ($\Omega \cdot m$), L is the length of the conductor (m), and A is the cross-sectional area of the conductor ($m^2$). The above equation may also be rearranged and expressed in terms of resistivity $\rho$, wherein $$\rho = \frac{RA}{L}.$$

The relationship between resistance R and temperature T may be expressed via the following linear approximation, $$R(T)=R_0[1+\alpha(T-T_0)],$$

where α is the temperature coefficient of resistance, $T_0$ is a fixed reference temperature (e.g., room temperature), and $R_0$ is the resistance at temperature $T_0$. The parameter α is an empirical parameter that is based on measurement data and may be different for different reference temperatures.

Similarly, the relationship between resistivity ρ and temperature T may be expressed via the following linear approximation, $$\rho(T)=\rho_0[1+\alpha(T-T_0)]$$

where α is the temperature coefficient of resistivity, $T_0$ is a fixed reference temperature (e.g., room temperature), and $\rho_0$ is the resistivity at temperature $T_0$. The parameter α is an empirical parameter that is based on measurement data and may be different for different reference temperatures.

Furthermore, for a metal, the relationship between resistivity ρ and temperature T may be expressed by the following Bloch-Grüneisen formula, $$\rho(T) = \rho(0) + A\left(\frac{T}{\Theta_R}\right)^n \int_0^{\frac{\Theta_R}{T}} \frac{x^n}{(e^x-1)(1-e^{-x})} dx,$$

where ρ(0) is the residual resistivity due to defect scattering, A is a constant that depends on the velocity of electrons at the Fermi surface, the Debye radius, and the number density of electrons in the metal. $\Theta_R$ is the Debye temperature as obtained from resistivity measurements and may match relatively closely with the values of Debye temperature obtained from specific heat measurements. n is an integer that depends upon the nature of interaction, with n=5 implying that the resistance is due to scattering of electrons by phonons (e.g., simple metals), n=3 implying that the resistance is due to s-d electron scattering (e.g. transition metals), and n=2 implying that the resistance is due to electron-electron interaction.

In another instance, the temperature of the heater structure (or the vicinity thereof) may be measured directly and monitored to mitigate the risk of overheating. In such a non-limiting embodiment, if the measured temperature is lower than the threshold temperature, then vaping will be permitted to continue as long as a signal continues to be received to activate the e-vapor device. On the other hand, if the measured temperature is equal to or higher than the threshold temperature, then the power to the vaporizer is stopped, and the e-vapor device will transition to standby mode.

In lieu of the above measurements (e.g., current, resistance, resistivity, temperature, etc.), the e-vapor device may be configured to transition to standby mode after a given number of puffs, which will indicate to an adult vaper that the existing capsule should be replaced with a new capsule. The appropriate quantity for the number of puffs (with which to program the e-vapor device) may be determined based on the average number of puffs needed by an adult vaper to deplete a capsule.

In another non-limiting embodiment, the e-vapor device may be configured to transition into standby mode after a given amount of time following the initiation of vaping. The appropriate amount of time (with which to program the e-vapor device) may be determined based on the average amount of time needed by an adult vaper to deplete a capsule.

In yet another non-limiting embodiment, the e-vapor device may be designed to passively reduce or prevent the occurrence of overheating. For example, the wick may be formed of a hydrophilic material that expands to a relatively large degree when saturated with the pre-vapor formulation. Conversely, the hydrophilic material may shrink considerably as the amount of pre-vapor formulation therein decreases below the saturated level. As a result, the wick can be configured to directly contact the heater structure when saturated (due to the increased size of the wick) and to reduce or avoid contact with the heater structure when less than saturated (e.g., due to the decreased size of the wick when the capsule is depleted). Alternatively, the hydrophilic material may be a separate component that is provided within the wick as a core so as to increase/decrease the size (e.g., diameter) of the wick.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An e-vapor device, comprising:
   a capsule configured to hold a pre-vapor formulation therein;
   a mouthpiece defining a vapor outlet and at least one downstream channel segment and configured to receive the capsule, the at least one downstream channel segment extending from a distal end of the mouthpiece to the vapor outlet; and
   a vaporizer including a heater structure and configured to engage with the mouthpiece to define a chamber for the capsule and to define at least one upstream channel segment around the chamber from the heater structure to at least one opening defined in a proximal end of the vaporizer, the at least one upstream channel segment configured to align with the at least one downstream channel segment of the mouthpiece when the mouthpiece is engaged with the vaporizer,
   the vaporizer configured to pierce the capsule to access the pre-vapor formulation therein, and to heat the pre-vapor formulation to generate a vapor.

2. The e-vapor device of claim 1, wherein the capsule is hermetically-sealed.

3. The e-vapor device of claim 1, wherein the capsule has an interior volume of 100 μL or less.

4. The e-vapor device of claim 1, wherein the capsule is configured to hold 100 mg or less of the pre-vapor formulation.

5. The e-vapor device of claim 1, wherein the capsule is spherically-shaped.

6. The e-vapor device of claim 1, wherein the capsule is in a form of a bead with an outer barrier formed of a food grade material.

7. The e-vapor device of claim 6, wherein the food grade material is silicone.

8. The e-vapor device of claim 1, wherein the capsule is conically-shaped.

9. The e-vapor device of claim 1, wherein the capsule is in a form of a pod with a puncture seal.

10. The e-vapor device of claim 1, wherein the mouthpiece includes a recess configured to receive the capsule.

11. The e-vapor device of claim 10, wherein the recess includes a concave surface that corresponds to an outer surface of the capsule.

12. The e-vapor device of claim 1, wherein the vaporizer includes a puncture device with a pointed, proximal end and an opposing distal end, the puncture device being a hollow, elongated structure defining a puncture device channel therein that extends from the pointed, proximal end to the opposing distal end.

13. The e-vapor device of claim 12, wherein the puncture device is configured to protract and pierce the capsule in response to the mouthpiece being engaged with the vaporizer and to retract in response to the mouthpiece being disengaged from the vaporizer.

14. The e-vapor device of claim 12, wherein the vaporizer includes a wick that extends through the puncture device channel from the pointed, proximal end to the opposing distal end of the puncture device.

15. The e-vapor device of claim 14, wherein end portions of the wick protrude from the pointed, proximal end of the puncture device.

16. The e-vapor device of claim 14, wherein the wick has a length of 15 mm or less.

17. The e-vapor device of claim 14, wherein the vaporizer includes a heater structure that is wrapped around a portion of the wick adjacent to the distal end of the puncture device.

18. The e-vapor device of claim 17, wherein the vaporizer is configured to cease a heating of the pre-vapor formulation while an activation signal is received by the vaporizer when a current in the heater structure is less than a reference level.

19. The e-vapor device of claim 1, further comprising:
a body section configured to engage with the vaporizer, the body section including a power source.

20. The e-vapor device of claim 1, wherein the vaporizer defines an upstream sector of the chamber, and the mouthpiece defines a downstream sector of the chamber.

* * * * *